United States Patent
Lutin

(10) Patent No.: US 6,645,532 B1
(45) Date of Patent: Nov. 11, 2003

(54) COMPOSITIONS AND METHOD FOR RELIEVING DISCOMFORT IN THE EARS

(76) Inventor: Matthew Lutin, 6938 Quiet Cove Dr., Carlsbad, CA (US) 92009

(*) Notice: Subject to any disclaimer, the term of this patent is extended or adjusted under 35 U.S.C. 154(b) by 0 days.

(21) Appl. No.: 09/487,482

(22) Filed: Jan. 19, 2000

Related U.S. Application Data

(60) Provisional application No. 60/116,342, filed on Jan. 19, 1999.

(51) Int. Cl.$^7$ .......................... A61K 33/14; A61K 9/08; A61M 31/00
(52) U.S. Cl. .................. 424/680; 424/677; 514/853; 514/872; 514/956; 514/957; 604/48; 604/500; 604/503; 604/514; 604/516
(58) Field of Search ................................. 424/680, 677; 514/853, 956, 872, 957; 604/48, 500, 514, 503, 516

(56) References Cited

U.S. PATENT DOCUMENTS 5,899,878 A * 5/1999 Glassman ..................... 604/48
6,182,660 B1 * 2/2001 Hopper .................. 128/207.13

FOREIGN PATENT DOCUMENTS

| CA | 1313142 | * | 1/1993 |
| WO | 97/29756 | * | 8/1997 |

OTHER PUBLICATIONS

Anonymous, 'ENTsol nasal lavage lets you breathe better, fast', Executive Health's Good Health Report, Aug. 1998, vol. 34, No. 11, p. 8 [retrieved on Jul. 24, 2000]. Retrieved from PROQUEST Direct on USTPO STIC NPL Virtual Library.*

Anonymous, 'Bradley Pharmaceuticals successively introduces ENTsol Drug–free hypertonic nasal wash: provides new therapy in fight against sinusitus', Business Wire [online], Nov. 19, 1998. New York, NY [retrieved on Jul. 24, 2000]. Retrieved from PROQUEST.*

Talbot, A. R. et al., "Mucociliary clearance and buffered hypertonic saline solution," The Laryngoscope, vol. 107, Apr. 1997, pp. 500–503.*

The Merck Manual of Medical Information, Home edition, Merck Research Laboratories, Whitehouse Station, NJ, 1997, pp. 1006–1007.*

MacMillan Health Encyclopedia, MacMillan Publishing Co., New York, NY, vol. 2, 1993, pp. 32–33.*

Dorland's Pocket Medical Dictionary, WB Saunder Co., Phila. (1982) pp313, 336.

* cited by examiner

Primary Examiner—John Pak
(74) Attorney, Agent, or Firm—Glenna Hendricks

(57) ABSTRACT

Generally, the method for preventing or relieving discomfort in the ears arising from congestion and/or obstruction of in the eustachian tubes comprising or changes in middle ear pressure relative to atmospheric pressure arising from environmental conditions in an individual need of prevention or relief from discomfort in the ears comprises the steps of: 1) administering a solution of 1.5%–3.5% (preferably 2–3%) sodium chloride solution having a pH of about 6 to 7.8 (preferably 6.5–7.5) in an aqueous solution as a spray or mist into the nose, 2) minimizing discharge of the solution from the nose for at least 5 seconds, then 3) evacuating the nose under pressure.

8 Claims, No Drawings

COMPOSITIONS AND METHOD FOR RELIEVING DISCOMFORT IN THE EARS

This application claim benefit of U.S. Provisional Application No. 60/116,342, filed Jan. 19, 1999.

FIELD OF THE INVENTION

This invention relates to the field of hypertonic solutions for delivery as sprays to relieve or prophylax against pain and discomfort in the ears arising from congestion or obstruction of the eustachian tubes or changes in middle ear pressure relative to atmospheric pressure from environmental conditions.

BACKGROUND OF THE INVENTION

The use of saline nose drops has been known. Several nose drops containing sodium chloride and other salts are available on the market. One commonly sold saline spray/drops preparation is LITTLE NOSES™, which contains 0.65% sodium chloride in water along with disodium phosphate, sodium phosphate, benzalkonium chloride and phenyl mercuric acetate 0.002% (a preservative). Another commonly used saline spray is Baby Ayr™, which contains, in addition to 0.65% sodium chloride, monobasic potassium phosphate/sodium hydroxide buffer to prevent nasal irritation. Neither of these preparation provide the level of clearing that is provided by the product described and claimed herein.

Baxter Healthcare Corporation sells two hypertonic solutions containing 3% and 5% sodium chloride for intravenous use to restore fluid and electrolyte balance. The solutions are used for replenishing sodium in patients who suffer from severe sodium depletion. The directions for administration include instructions to give slowly because of possible damage to the veins.

Recently, a composition containing hypertonic salt solutions called ENTsol™ has been placed on the market for use in reducing edema in the nasal passages. No teaching relating to relief from discomfort arising from congestion or changes of pressure in the eustachian tubes is taught therein, and the methods of administration taught in the instructions do not provide benefits associated with the methods taught herein.

SUMMARY OF THE INVENTION

This invention provides solutions containing at least 1.5% salt of a strong acid with preferred salt content at 2% to 3.5%, preferably 2%–3%. The most preferred compositions contain about 2.4–3% sodium chloride and are delivered in the form of sprays or mists. The methods of the invention are useful for treating and preventing discomfort in the ears that results from congestion in the eustachian tubes and/or pressure changes in the environment such as those caused by changes in altitude. Solutions for use in accord with the methods of the invention usually do not contain alcohol.

DETAILED DESCRIPTION OF THE INVENTION

The instant invention relates to use of hypertonic salt solutions for use in decongesting and clearing the eustachian tubes and for equalizing pressure in the middle ear relative to atmospheric pressure. It has now been found that compositions containing at least 1.5% of a soluble salt of a strong acid are of particular value. The preferred salt is sodium chloride. The methods of the invention provide relief from discomfort in the ears due to congestion in the eustachian tubes or any changes in pressure in the inner ear relative to atmospheric pressure. The preparations are buffered as necessary to provide the appropriate pH of 6 to 7.8, with preferred pH being between 6.5 and 7.5, with compositions having pH 7–7.5 being more common. In addition, compositions of the invention may contain other agents such as preservatives, odorants, stabilizers (including antioxidants), colorants, and other additives used in preparations administered into the upper respiratory tract or the oral cavity. Of course other medicinal agents may be added to the compositions for purposes of alleviating other maladies. Such agents may include, for example, analgesics, antibacterial agents and emollients.

Some of the appropriate buffer systems for use in practice of the invention include citric acid-citrate salts, acetic acid-acetate salts, and benzoic acid-benzoic salt systems. However, any buffer system commonly used for preparing medicinal compositions would be appropriate. Suitable preservatives include, but are not limited to, butylated hydroxyanisole (BHA), butylated hydroxytoluene (BHT), benzoic acid, phenyl mercuric acetate and ascorbic acid. When practicing the method of this invention, the solutions are not immediately expelled from the nose. It is essential that any additives be non-irritating, since the solution, when used in the method taught herein, is in contact with the orifice to the eustachian tubes.

The form in which the salt used or is added to the solution does not matter so long as the salt is solubilized. For example, coarse sea salt or regular table salt (preferably without additives) may be used in preparation of the compositions to be administered in accord with the teachings herein.

The method of administration requires that the solution sprayed into the nose not be discharged immediately, but be allowed to remain in contact with target mucosa for 5 to 45 seconds, then be forced from the nose. Generally, the method for preventing or relieving discomfort in the ears arising from congestion and/or obstruction of in the eustachian tubes comprising or changes in middle ear pressure relative to atmospheric pressure arising from environmental conditions in an individual need of prevention or relief from discomfort in the ears comprises the steps of: 1) administering a solution of 1.5%–3.5% (preferably 2–3%) sodium chloride solution having a pH of about 6 to 7.8 (preferably 6.5–7.5) in an aqueous solution as a spray or mist into the nose, 2) minimizing discharge of the solution from the nose for at least 5 seconds, then 3) evacuating the nose under pressure. Blowing the nose after the solution has been in contact with the orifice to the eustachian tube appears to equalize the pressure in the middle ear and the atmosphere, and is an important part of the treatment or prophylaxis of discomfort. The minimization of discharge of solution in step 2 may be accomplished by, for example, holding the nose closed or by simply not moving in such a manner as to expel the solution. The process is repeated in each nostril.

The methods of the invention are useful for treating or prophylaxing against discomfort in the ears arising from changes in altitude. Some examples of activities that give rise to such changes are skiing, water and sky diving, riding in aircraft or driving in mountainous areas. Practice of the methods of the invention before undertaking such activities appears to be beneficial. Furthermore, the method of the invention can be practiced without access to a receptacle such as a sink, which is required if salt solutions are used as a wash. Hence, the practice of the invention during such activities as air travel or skiing is appropriate.

In a preparation for administration in accord with the teaching herein, 2.5 grams of salt is added to 100 ml of water. The preparation is tested for pH. The pH is then adjusted with base or acid such as dilute sodium hydroxide or citric acid to provide a pH of 7 to 7.5. The formulation is placed in a bottle having a first covering means, said covering means having an opening through which a spray can be expelled when the compressible bottle is squeezed. A conduit for passage of solution extends downward into the bottle and upward to the opening in the covering means. A second covering means is then placed over the first covering means to prevent contamination of the contents of the bottle.

In a second preparation, 2.45 grams of sodium chloride is added to 100 ml of water. The preparation is adjusted to a pH of 7.5 in the manner described above. The formulation is placed in a bottle having a covering means with an atomizing means as an integral part of said covering means.

A composition was prepared containing the following:

| Ingredient | Amount in 1 liter |
| --- | --- |
| Sodium Chloride, USP | 25.0 g |
| Monobasic Sodium Phosphate (Anhydrous USP) | 1.6 g |
| Dibasic Sodium Phosphate (Anhydrous USP) | 7.57 g |
| Benzlkonium Chloride USP | 0.05 g |
| Purified water USP | q.s to 1.0 liter |

This formulation yields a product with a pH of about 7.4. The formulation has minimal taste or color and is non-irritating.

From about 0.1 to 3 ml (preferably about 0.5 to 2 ml.) may be introduced into the nose at one time. It is believed that this amount is sufficient to saturate the mucosa at the eustachian tube orifice. When the compositions are administered as a spray or mist, the solution is sprayed into the nose. It is sometimes helpful to inhale while the solution is being introduced. One should attempt to avoid sneezing, blowing the nose or exhaling with such pressure as to expel the solution immediately after administration. If the individual, such as a small child, is unable to cooperate by blowing the solution from the nose, other means of exerting the necessary pressure are appropriate. The method is most effective if the solution is not expelled for about 15–45 seconds after administration. The nose can then be evacuated and the process repeated up to 4 times as needed.

Compositions of the invention will not cause irritation when used as directed. However, persons on a low salt or low sodium diet should discuss with their primary care physician any instillation of the compositions into the nose or nasopharynx, since the salt present may be inappropriate with their medical treatment.

It is interesting to note that the use of the hypertonic solution, when administered as a spray or mist in accord with the teaching herein can relieve discomfort that arises in the ears because of changes in pressure even when the method practiced a short time before the individual is exposed to the changes in pressure that might give rise to discomfort.

What is claimed is:

1. A method of prophylaxing against or relieving discomfort in the ears arising from congestion and/or obstruction of the eustachian tubes or changes in middle ear pressure relative to atmospheric pressure arising from changes in altitude in an individual in need thereof a comprising the steps of:

1) administering an aqueous solution of 2% to 3% w/v of sodium chloride, said solution having a pH of 6 to 7.8, into the nose, 2) minimizing discharge of the solution from the nose for at least 5 seconds, then 3) expelling the solution from the nose under pressure.

2. A method of claim 1 wherein the solution contains sodium chloride concentration of 2.4% to 3% w/v.

3. A method of claim 1 wherein the solution is in a compressible bottle having a covering means, said covering means having an opening appropriate for expelling solution as a spray.

4. A method of claim 1 wherein the solution is in a container with an atomizer.

5. A method of claim 1 wherein the solution contains sodium chloride concentration of 2.4% to 2.6% w/v.

6. A method of claim 1 wherein the sodium chloride is at 2.4%–2.6% w/v concentration and pH is within the range of 6.5 to 7.5.

7. A method of claim 6 wherein the pH of the solution is within the range of 7–7.5.

8. The method of claim 1 wherein, in step 2 the discharge of the sprayed solution from the nose is minimized for 15–45 seconds.

* * * * *